(12) United States Patent
Tajima

(10) Patent No.: US 12,121,387 B2
(45) Date of Patent: Oct. 22, 2024

(54) RADIATION DETECTION DEVICE, AND OPERATION METHOD AND OPERATION PROGRAM THEREOF

(71) Applicant: FUJIFILM CORPORATION, Tokyo (JP)

(72) Inventor: Takashi Tajima, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 170 days.

(21) Appl. No.: 18/045,467

(22) Filed: Oct. 11, 2022

(65) Prior Publication Data

US 2023/0122938 A1 Apr. 20, 2023

(30) Foreign Application Priority Data

Oct. 18, 2021 (JP) ................................ 2021-170423

(51) Int. Cl.
*A61B 6/00* (2024.01)
*A61B 6/42* (2024.01)
*A61B 6/46* (2024.01)

(52) U.S. Cl.
CPC .............. *A61B 6/5258* (2013.01); *A61B 6/52* (2013.01); *A61B 6/4208* (2013.01); *A61B 6/461* (2013.01)

(58) Field of Classification Search
CPC ................................................... A61B 6/5258
See application file for complete search history.

(56) References Cited

U.S. PATENT DOCUMENTS

| 2010/0020933 A1* | 1/2010 | Topfer | H04N 5/16 382/130 |
| 2013/0169784 A1* | 7/2013 | Iwashita | H04N 25/626 348/77 |
| 2015/0131785 A1* | 5/2015 | Topfer | G06T 5/70 378/98 |

FOREIGN PATENT DOCUMENTS

JP 2016-201634 A 12/2016

OTHER PUBLICATIONS

CN 106073809 A and its English translation (Year: 2016).*

* cited by examiner

*Primary Examiner* — Chih-Cheng Kao
(74) *Attorney, Agent, or Firm* — SOLARIS Intellectual Property Group, PLLC

(57) ABSTRACT

An average offset image is acquired without irradiation of a radiation. A first image is acquired when a first time elapses from continuous irradiation with the radiation for imaging a subject on a pixel region. A second image is acquired when a second time longer than the first time elapses from an end of the continuous irradiation. The irradiation with the radiation for imaging the subject is performed on the pixel region after an elapse of the second time from the end of the continuous irradiation and a pixel signal from the pixel region is read out to acquire a radiographic image. An offset image representing an offset component and an afterimage representing an afterimage component according to a time of the continuous irradiation, the first time, the second time, and a defined time are generated based on the first image, the second image, and the average offset image.

12 Claims, 14 Drawing Sheets

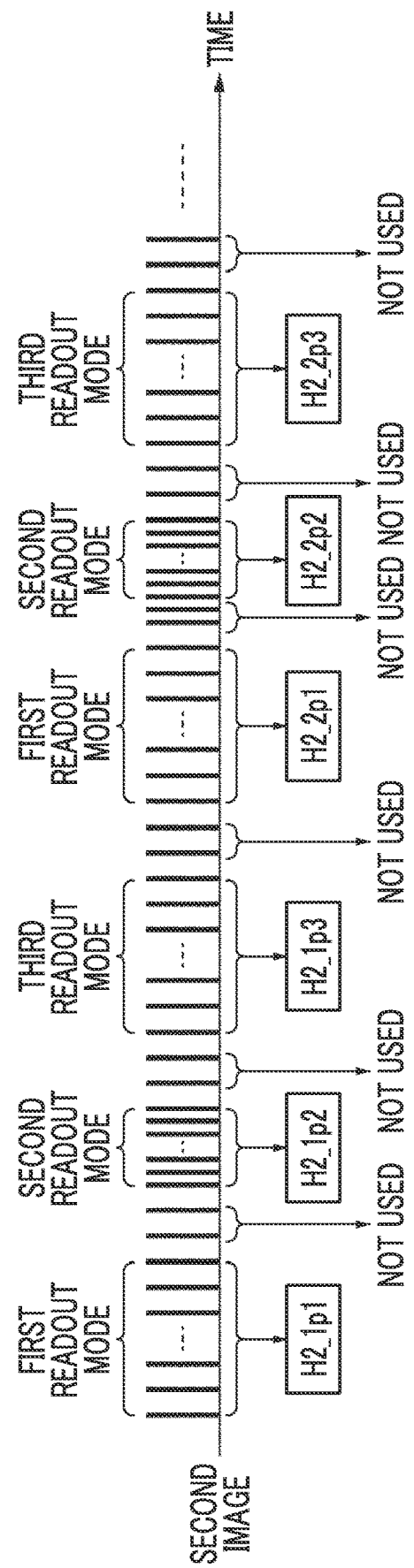

RADIATION DETECTION DEVICE, AND OPERATION METHOD AND OPERATION PROGRAM THEREOF

CROSS REFERENCE TO RELATED APPLICATIONS

The present application claims priority under 35 U.S.C. § 119 to Japanese Patent Application No. 2021-170423 filed on Oct. 18, 2021. The above application is hereby expressly incorporated by reference, in its entirety, into the present application.

BACKGROUND

Technical Field

A technique of the present disclosure relates to a radiation detection device, and an operation method and operation program thereof.

Related Art

In a medical field, an X-ray imaging system using, for example, an X-ray as a radiation is known. The X-ray imaging system is configured of an X-ray source that generates the X-ray, an X-ray detector that detects an X-ray image based on the X-ray transmitted through a subject, and a console that performs drive control of the X-ray image detector, storage and display of the X-ray image, and the like.

For the X-ray detector, there are a direct conversion method of converting the X-ray into a direct charge and an indirect conversion method of converting the X-ray into visible light and then converting the visible light into a charge. In any of the methods, the X-ray detector has a pixel region in which a plurality of pixels for detecting the X-ray are arranged and a readout unit that reads out a pixel signal from the pixel region, and generates an X-ray image based on the pixel signal read out by the readout unit.

The X-ray image detected by the X-ray detector includes dark current noise generated in each pixel, fixed pattern noise generated by a charge amplifier included in the readout unit, and the like. In order to remove such a noise component from the X-ray image, offset data is acquired in advance prior to X-ray imaging. The pixel signal is read out from the pixel region in a state where the X-ray is not irradiated to acquire the offset data. The offset data includes only the noise component. After the offset data is acquired, offset correction is performed by subtracting the offset data from the X-ray image obtained by the X-ray imaging to obtain an X-ray image from which the noise has been removed. Various methods for performing such offset correction have been proposed (refer to, for example, JP2016-201634A). In order to further improve the accuracy of the offset correction, it has been proposed to use an average value of a plurality of pieces of offset data obtained by acquiring the offset data a plurality of times for the offset correction. With the averaging of the plurality of pieces of offset data, random noise is reduced.

By the way, there is a case where perspective imaging is performed in which the subject is continuously irradiated with the X-ray and a perspective image acquired by the continuous irradiation is displayed in real time. In a case where the perspective imaging is performed, the offset data cannot be acquired since the subject is continuously irradiated with the X-ray. Further, in a case where imaging is continued from previous imaging, the X-ray image also includes noise due to an afterimage (lag) of the X-ray irradiated during the previous imaging. The lag may occur in the X-ray detector employing any method of the direct conversion method or the indirect conversion method. In the case of the indirect conversion method, the lag is a phenomenon that occurs in a case where the emission characteristics of a scintillator layer that converts the X-ray into visible light change with large energy of the incident X-ray and influence of the previous X-ray imaging remains in the scintillator layer until the next X-ray imaging.

The lag has different attenuation behaviors according to a continuous irradiation time of the X-ray and an elapsed time from an end of the continuous irradiation. A dark current is a noise component generated in a state where the X-ray is not irradiated and is mainly generated due to heat. The dark current also has different increase or decrease behaviors according to the continuous irradiation time of the X-ray and the elapsed time from an end of the continuous irradiation. Therefore, it is necessary to correct the X-ray image in consideration of each of an offset component which is a noise component based on the dark current or the like and a lag component which is a noise component based on the lag.

SUMMARY OF THE INVENTION

The present disclosure has been made in view of the above circumstances, and an object of the present disclosure is to improve accuracy of offset correction and to suppress influence of an afterimage.

A radiation detection device according to the present disclosure comprises a pixel region in which a plurality of pixels for detecting a radiation are arranged, a readout unit that reads out a pixel signal from the pixel region, and at least one processor.

The processor is configured to average a plurality of images acquired by reading out a pixel signal from the pixel region a plurality of times in a state where irradiation with the radiation is not performed to acquire an average offset image, perform continuous irradiation with the radiation for imaging a subject on the pixel region and read out the pixel signal from the pixel region when a first time elapses from an end of the continuous irradiation to acquire a first image, read out the pixel signal from the pixel region when a second time longer than the first time elapses from the end of the continuous irradiation to acquire a second image, perform irradiation with the radiation for imaging the subject on the pixel region after an elapse of a defined time from the end of the continuous irradiation and read out the pixel signal from the pixel region to acquire a radiographic image, and generate an offset image representing an offset component and an afterimage image representing an afterimage component according to a time of the continuous irradiation, the first time, the second time, and the defined time, based on the first image, the second image, and the average offset image.

In the radiation detection device according to the present disclosure, the processor repeatedly reads out the pixel signal from the pixel region after the acquisition of the first image to update the second image, and generates the offset image and the afterimage image according to the time of the continuous irradiation, the first time, an updated second time until the updated second image is acquired from the end of the continuous irradiation, and the defined time, based on the first image, the updated second image, and the average offset image.

In the radiation detection device according to the present disclosure, the processor may continuously update the second image until a third time longer than the second time elapses from the end of the continuous irradiation, stop the update of the second image until a fourth time longer than the third time elapses after the elapse of the third time, restart the update of the second image after the elapse of the fourth time, update the second image until a fifth time longer than the fourth time elapses, and stop the acquisition of the second image after the elapse of the fifth time to update the average offset image.

In the radiation detection device according to the present disclosure, the processor may generate the offset image and the afterimage image according to the time of the continuous irradiation, the first time, the second time, and the defined time, based on the first image, the second image, and the average offset image, in a case where the defined time is the fourth time or less, and generate the offset image based on the second image and the average offset image in a case where the defined time exceeds the fourth time and is the fifth time or less.

In the radiation detection device according to the present disclosure, the processor may correct the radiographic image based on the average offset image, the offset image, and the afterimage image to generate a corrected radiographic image in a case where the defined time is the fourth time or less, correct the radiographic image based on the average offset image and the afterimage image to generate a corrected radiographic image in a case where the defined time exceeds the fourth time and is the fifth time or less, and correct the radiographic image based on the average offset image to generate a corrected radiographic image in a case where the defined time exceeds the fifth time.

In the radiation detection device according to the present disclosure, the processor may output the corrected radiographic image for display.

In the radiation detection device according to the present disclosure, in a case where a plurality of readout modes in which a readout rate of the pixel signal and a readout method of the pixel signal from the pixel region are different from each other are set, the processor may continuously acquire the average offset image corresponding to each of the plurality of readout modes while switching the plurality of readout modes, continuously acquire the first image corresponding to each of the plurality of readout modes while switching the plurality of readout modes, and update the second image corresponding to each of the plurality of readout modes while switching the plurality of readout modes after the acquisition of the first image.

In the radiation detection device according to the present disclosure, the processor may continuously acquire the first image while switching the plurality of readout modes in order from a readout mode used in previous radiation irradiation among the plurality of readout modes.

In the radiation detection device according to the present disclosure, the processor may acquire the first image and the second image by using a pixel signal other than the pixel signal read out from the pixel region at the time of switching the readout mode.

In the radiation detection device according to the present disclosure, the processor may read out pixel signals from the pixel region a plurality of first number of times before and after the first time and average the pixel signals read out the first number of times to acquire the first image, and read out pixel signals from the pixel region a second number of times larger than the first number of times before and after the second time and average the pixel signals read out the second number of times to acquire the second image.

An operation method of a radiation detection device according to the present disclosure is an operation method of a radiation detection device including a pixel region in which a plurality of pixels for detecting a radiation are arranged, and a readout unit that reads out a pixel signal from the pixel region.

The operation method comprises averaging a plurality of images acquired by reading out a pixel signal from the pixel region a plurality of times in a state where irradiation with the radiation is not performed to acquire an average offset image, performing continuous irradiation with the radiation for imaging a subject on the pixel region and reading out the pixel signal from the pixel region when a first time elapses from an end of the continuous irradiation to acquire a first image, reading out the pixel signal from the pixel region when a second time longer than the first time elapses from the end of the continuous irradiation to acquire a second image, performing irradiation with the radiation for imaging the subject on the pixel region after an elapse of a defined time from the end of the continuous irradiation and reading out the pixel signal from the pixel region to acquire a radiographic image, and generating an offset image representing an offset component and an afterimage image representing an afterimage component according to a time of the continuous irradiation, the first time, the second time, and the defined time, based on the first image, the second image, and the average offset image.

An operation program in a radiation detection device according to the present disclosure is an operation program for causing a computer to execute an operation method in a radiation detection device including a pixel region in which a plurality of pixels for detecting a radiation are arranged, and a readout unit that reads out a pixel signal from the pixel region.

The operation program for causing the computer to execute a procedure of averaging a plurality of images acquired by reading out a pixel signal from the pixel region a plurality of times in a state where irradiation with the radiation is not performed to acquire an average offset image, a procedure of performing continuous irradiation with the radiation for imaging a subject on the pixel region and reading out the pixel signal from the pixel region when a first time elapses from an end of the continuous irradiation to acquire a first image, a procedure of reading out the pixel signal from the pixel region when a second time longer than the first time elapses from the end of the continuous irradiation to acquire a second image, a procedure of performing irradiation with the radiation for imaging the subject on the pixel region after an elapse of a defined time from the end of the continuous irradiation and reading out the pixel signal from the pixel region to acquire a radiographic image, and a procedure of generating an offset image representing an offset component and an afterimage image representing an afterimage component according to a time of the continuous irradiation, the first time, the second time, and the defined time, based on the first image, the second image, and the average offset image.

According to the technique of the present disclosure, it is possible to improve the accuracy of the offset correction and to suppress the influence of the afterimage.

BRIEF DESCRIPTION OF THE DRAWINGS

FIG. 15 is a diagram for describing a timing of acquiring a second image while switching a plurality of readout modes.

DETAILED DESCRIPTION

Figure 1:
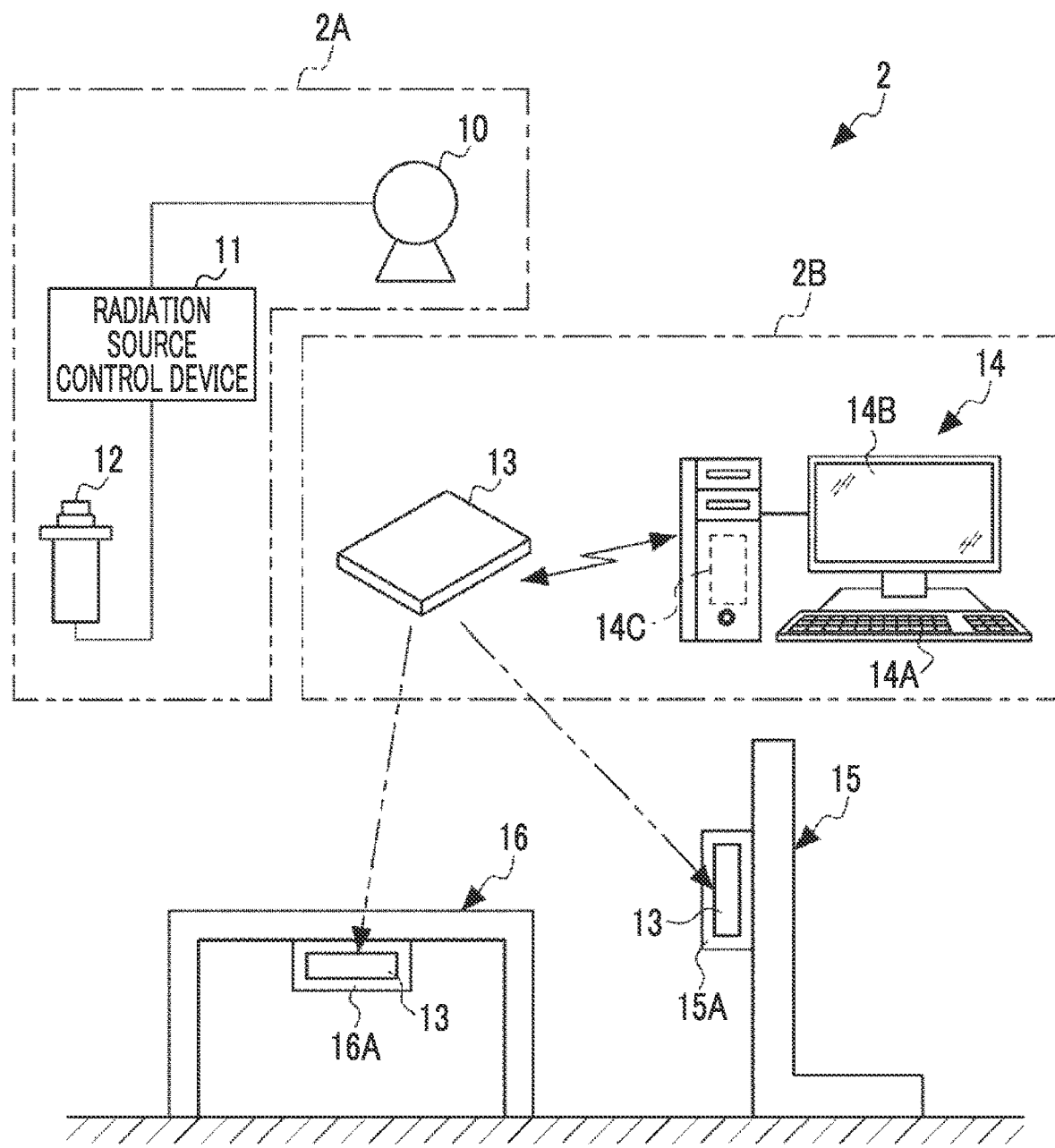
FIG. 1 is a schematic diagram showing a configuration of an X-ray imaging system.

Hereinafter, an embodiment of the present disclosure will be described with reference to drawings. FIG. 1 is a schematic configuration diagram of an X-ray imaging system to which a radiation detection device according to the embodiment of the present disclosure is applied. As shown in FIG. 1, an X-ray imaging system 2 is configured of an X-ray irradiation device 2A and an X-ray imaging device 2B.

The X-ray irradiation device 2A has an X-ray source 10, a radiation source control device 11, and an irradiation switch 12. The X-ray source 10 has an X-ray tube and an irradiation field limiter (collimator) that limits an irradiation field of the X-ray irradiated by the X-ray tube. The radiation source control device 11 controls an operation of the X-ray source 10. The irradiation switch 12 instructs the X-ray source 10 to start the X-ray irradiation in response to an operation by an operator such as a radiologist. The X-ray is an example of a radiation of the present disclosure. In the X-ray imaging system 2 according to the present embodiment, perspective imaging is performed in which the subject is continuously irradiated with the X-ray and X-ray images are sequentially acquired at a predetermined frame rate and readout method during the continuous irradiation.

The X-ray imaging device 2B has an electronic cassette 13 and a console 14. The electronic cassette 13 is a portable X-ray detector. The console 14 performs operation control of the electronic cassette 13 and display processing of the X-ray image. Further, the X-ray imaging system 2 is provided with an upright imaging stand 15, a decubitus imaging table 16, or the like. The upright imaging stand 15 is used for imaging the subject in a standing posture. The decubitus imaging table 16 is used for imaging the subject in a decubitus position. The electronic cassette 13 is detachably set in a holder 15A of the upright imaging stand 15 or a holder 16A of the decubitus imaging table 16. The X-ray image is an example of a radiographic image of the present disclosure. Further, the electronic cassette 13 is an example of a radiation detection device of the present disclosure.

The X-ray irradiation device 2A is not electrically connected to the X-ray imaging device 2B. That is, the X-ray imaging device 2B is not a synchronous type in which the electronic cassette 13 is operated in synchronization with the start of the X-ray irradiation, but an asynchronous type. Therefore, the electronic cassette 13 is provided with a function of performing irradiation start detection for detecting that the X-ray irradiation has been started by the X-ray irradiation device 2A.

The console 14 is communicably connected to the electronic cassette 13 by a wired method or a wireless method. The console 14 controls the operation of the electronic cassette 13 in response to an input operation of the operator via an input device 14A such as a keyboard. The X-ray image acquired by the electronic cassette 13 is output to the console 14 for display and displayed on a display 14B provided on the console 14. Further, the X-ray image is stored in a storage device 14C, such as a hard disk or a flash memory, built in the console 14 or an image accumulation server (not shown) connected to the console 14 via a network.

Figure 2:
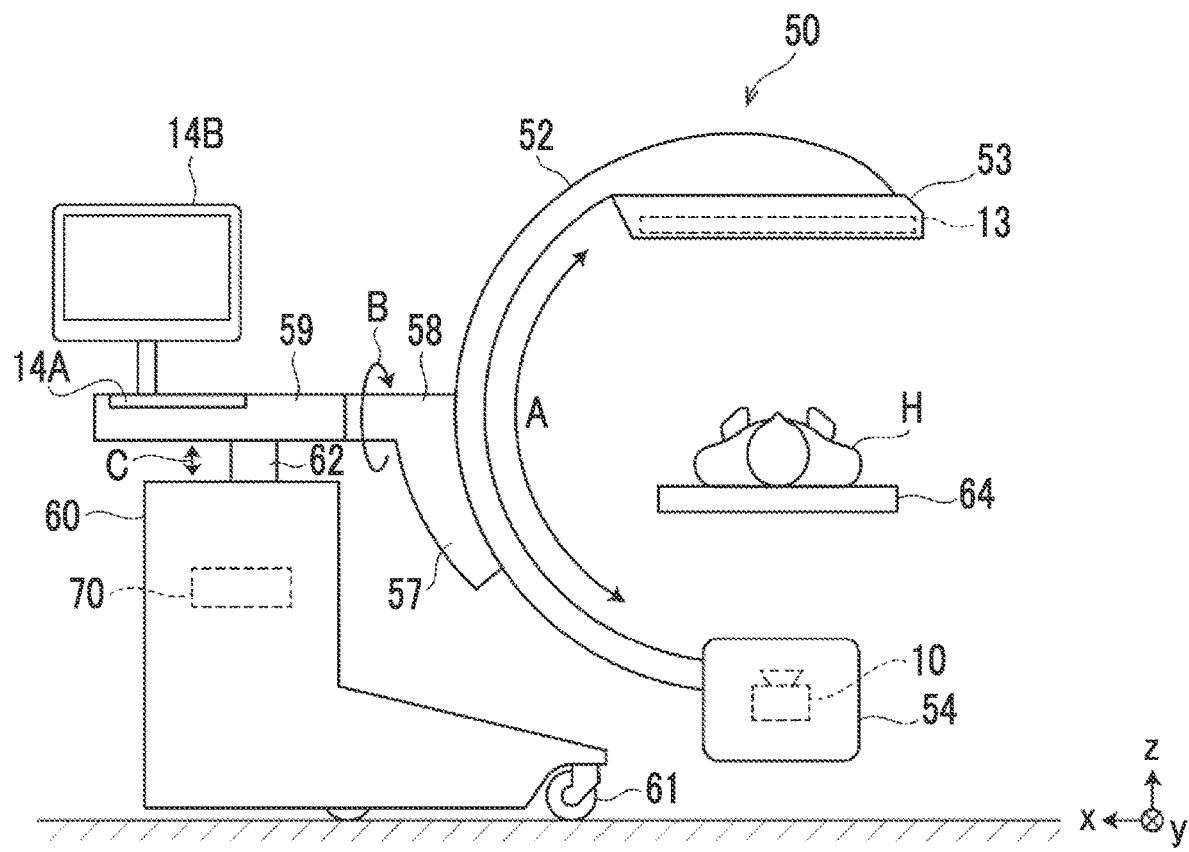
FIG. 2 is a diagram showing an X-ray perspective imaging device provided with a C-arm.

As the X-ray imaging system according to the present embodiment, an X-ray perspective imaging device provided with a C-arm suitable for the perspective imaging may be used. FIG. 2 is a diagram showing the X-ray perspective imaging device provided with the C-arm. In FIG. 2, the same reference number is assigned to the same configuration as in FIG. 1, and detailed description thereof will be omitted.

An X-ray perspective imaging device 50 shown in FIG. 2 comprises a C-arm 52. An imaging unit 53 is attached to one end portion of the C-arm 52, and an X-ray irradiation unit 54 is attached to the other end portion of the C-arm 52 so as to face the imaging unit 53. An electronic cassette 13 is accommodated inside the imaging unit 53. The X-ray irradiation unit 54 corresponds to the X-ray irradiation device 2A shown in FIG. 1, and the X-ray source 10 is accommodated therein.

The C-arm 52 is movably held by a C-arm holding part 57 in an arrow A direction shown in FIG. 2 such that angles of the imaging unit 53 and the X-ray irradiation unit 54 with respect to a z direction (vertical direction) shown in FIG. 2 can be integrally changed. Further, the C-arm holding part 57 has a shaft part 58, and the shaft part 58 rotatably connects the C-arm 52 to a bearing 59. Accordingly, the C-arm 52 is rotatable about the shaft part 58 as a rotation axis in an arrow B direction shown in FIG. 2.

The X-ray perspective imaging device 50 comprises a body part 60. A plurality of wheels 61 are attached to a bottom portion of the body part 60, and the wheels enable the X-ray perspective imaging device 50 to be moved. A support shaft 62 that expands and contracts in the z-axis direction of FIG. 2 is provided in an upper portion of a housing of the body part 60 in FIG. 2. The bearing 59 is movably held in an upper portion of the support shaft 62 in an arrow C direction. A control unit 70 corresponding to the console 14 is accommodated inside the body part 60. Further, the input device 14A and the display 14B are provided in the upper portion of the body part 60.

Since the X-ray perspective imaging device 50 has the above-described configuration, a subject H is irradiated with the radiation from below the subject H lying on an imaging table 64, the radiation transmitted through the subject H is detected by the electronic cassette 13 of the imaging unit 53, and an X-ray image of the subject H is acquired. The C-arm 52 is movable in the arrow A direction, the arrow B direction, and the arrow C direction, and the X-ray perspective imaging device 50 is movable by the wheels 61. Therefore, the X-ray perspective imaging device 50 shown in FIG. 2 can image a desired site of the subject H lying on the imaging table 64 from a desired direction.

Figure 3:
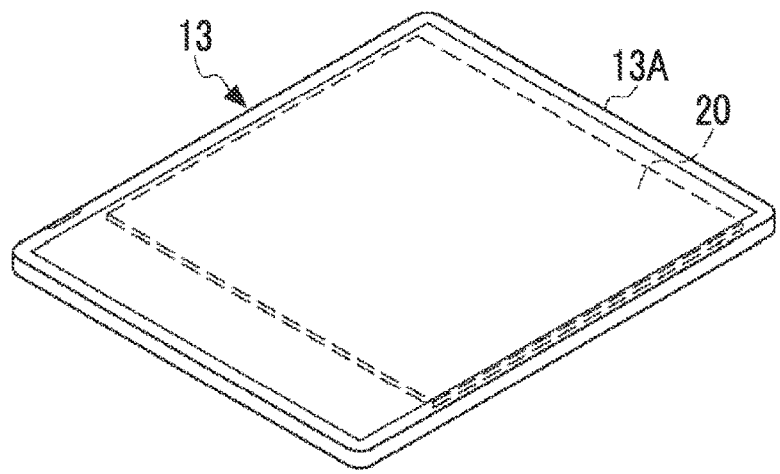
FIG. 3 is a perspective view of an electronic cassette.

FIG. 3 is a perspective view of the electronic cassette. As shown in FIG. 3, the electronic cassette 13 is configured of an image detection unit 20 and a housing 13A. The housing 13A has a flat box shape and accommodates the image detection unit 20 therein. A battery (for example, secondary battery) that supplies power for driving the electronic cassette 13 and an antenna for performing wireless communication with the console 14 are built in the housing 13A.

Figure 4:
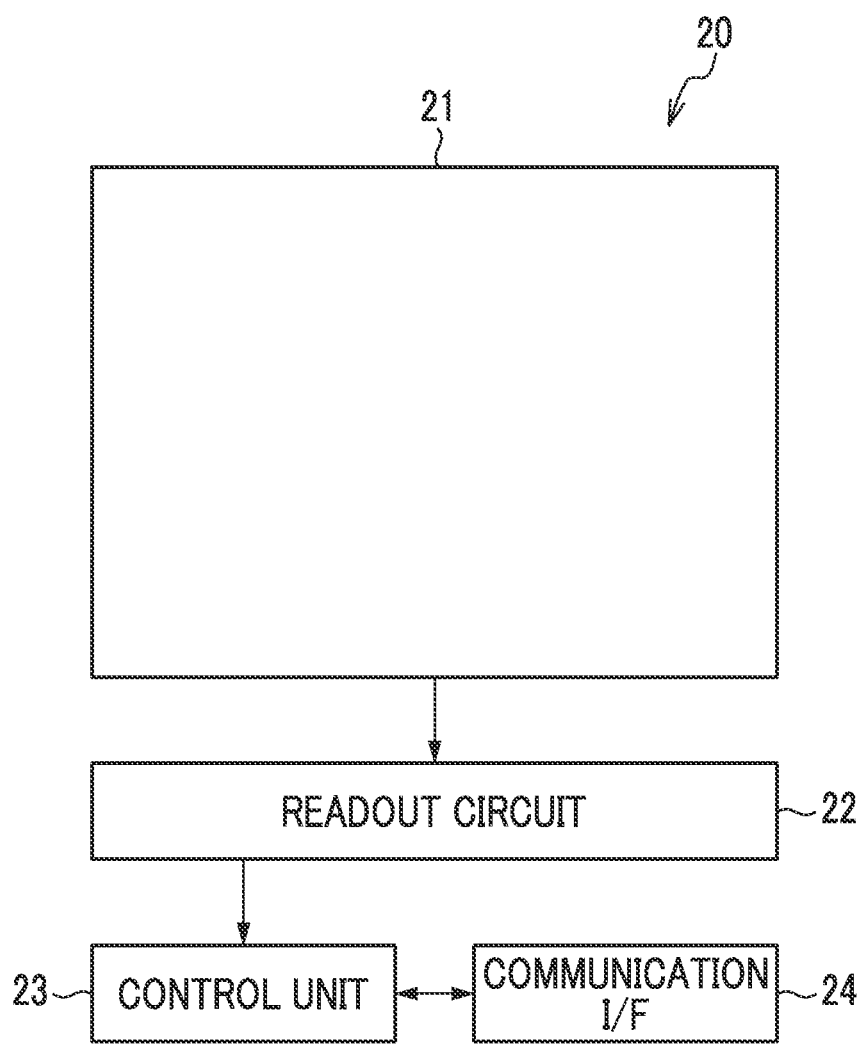
FIG. 4 is a schematic diagram showing a configuration of an image detection unit.

FIG. 4 is a schematic diagram showing a configuration of the image detection unit. As shown in FIG. 4, the image detection unit 20 is configured of a pixel region 21, a readout circuit 22, a control unit 23, and a communication interface (I/F) 24.

The pixel region 21 is formed on a thin film transistor (TFT) active matrix substrate. A plurality of pixels arranged on a matrix along an X direction and a Y direction orthogonal to each other are included. The pixel is an element that generates and accumulates charges according to an incident light amount of the X-ray.

The image detection unit 20 can repeatedly record and read out the X-ray image, and may be a so-called direct type in which the X-ray is directly converted into the charge or may be a so-called indirect type in which the X-ray is temporarily converted into visible light and the visible light is converted into a charge signal. Further, as a method of reading out a radiographic image signal, a so-called TFT readout method in which an image signal is read out by turning a TFT switch on and off is employed.

The readout circuit 22 reads out the charges accumulated in each pixel of the pixel region 21 by a predetermined readout rate and readout method. The readout rate depends on a frame rate of the X-ray image, and values such as 7.5 fps, 15 fps, and 30 fps are used. As the readout method, a method of reading out a pixel signal from each of the respective pixels, a binning readout method of adding and reading out the charges accumulated in the plurality of pixels, and the like are used. Hereinafter, the readout rate and the readout method are referred to as a readout mode.

The readout circuit 22 comprises a charge amplifier that converts the charge signal read out from the pixel region 21 into a voltage signal, a sampling two correlation pile circuit that samples the voltage signal output from the charge amplifier, an analog-to-digital (AD) conversion unit that converts the voltage signal into a digital signal, and the like. The readout circuit 22 outputs the pixel signal read out from each pixel of the pixel region 21 to the control unit 23. The pixel signal corresponds to an incident amount of the X-ray read out from the pixel region 21. The pixel signal for one frame read out from each pixel of the pixel region 21 constitutes the X-ray image. The readout circuit 22 is an example of a readout unit of the present disclosure.

The control unit 23 performs X-ray imaging processing by controlling an operation of reading out the pixel signal from the pixel region 21 by the readout circuit 22 and performs acquisition processing of the X-ray image based on the readout pixel signal. Further, the control unit 23 performs image acquisition processing of acquiring an image for correcting the X-ray image and correction processing of correcting the X-ray image based on the acquired image.

The communication I/F 24 is connected to the console 14 (refer to FIG. 1) by wire or wirelessly and transmits and receives data to and from the console 14. The communication I/F 24 performs reception of data including an imaging condition transmitted from the console 14, transmission of data representing the X-ray image generated by the control unit 23 to the console 14, and the like.

Figure 5:
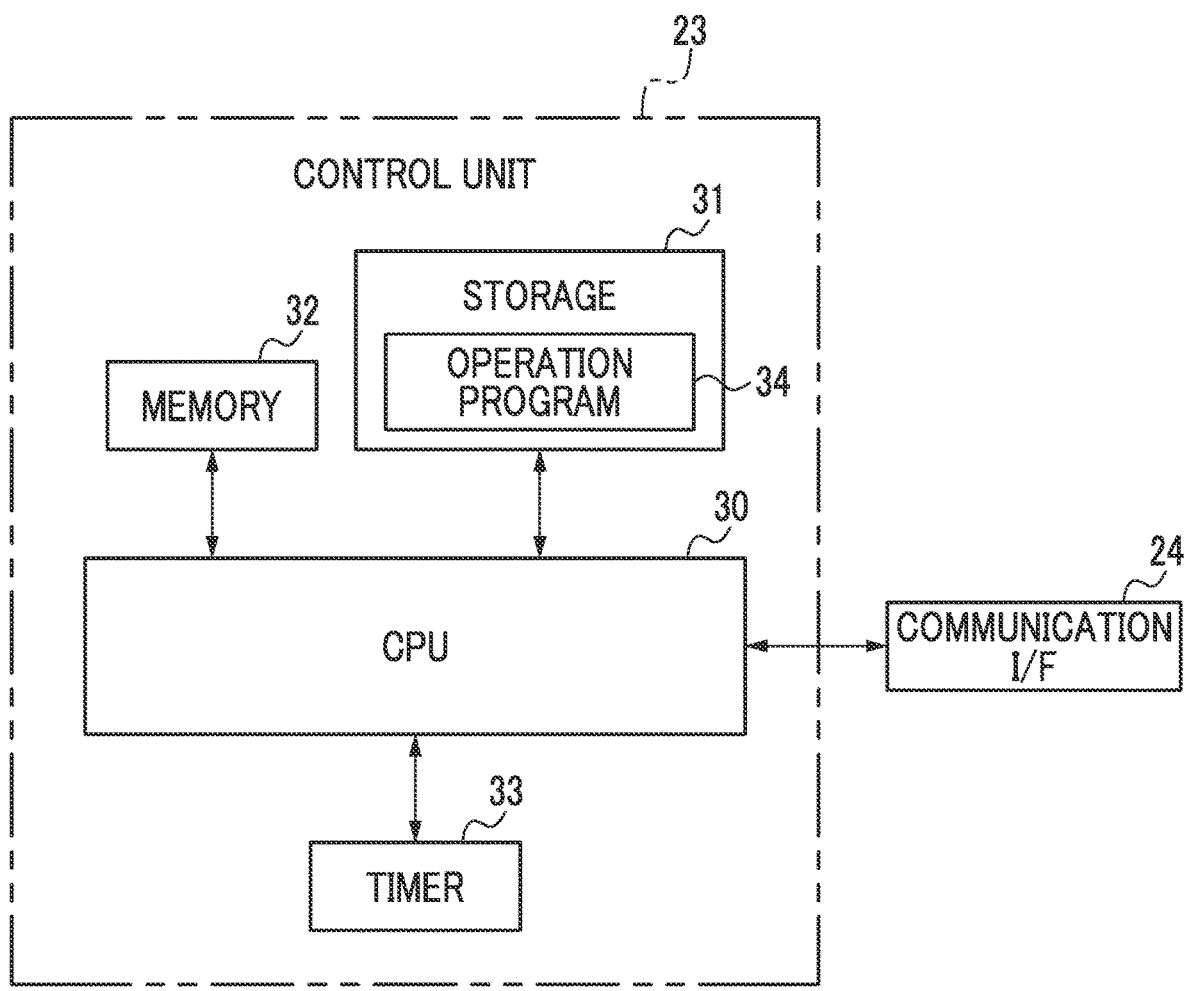
FIG. 5 is a block diagram showing a configuration of a control unit of the image detection unit.

FIG. 5 is a schematic block diagram showing a configuration of the control unit of the image detection unit. As shown in FIG. 5, the control unit 23 is configured of, for example, a central processing unit (CPU) 30, a storage 31, a memory 32, a timer 33, and the like. The storage 31 stores an operation program 34 and various types of data. The storage 31 is a non-volatile storage device such as a flash memory. The memory 32 is a volatile storage device such as a random access memory (DRAM) and is used as a work memory. The timer 33 is a timing device that measures time such as an irradiation time and a timing of reading out the pixel signal. The CPU 30 operates each unit based on the operation program 34 to realize various functions. The CPU 30 is an example of a processor of the present disclosure.

Figure 6:
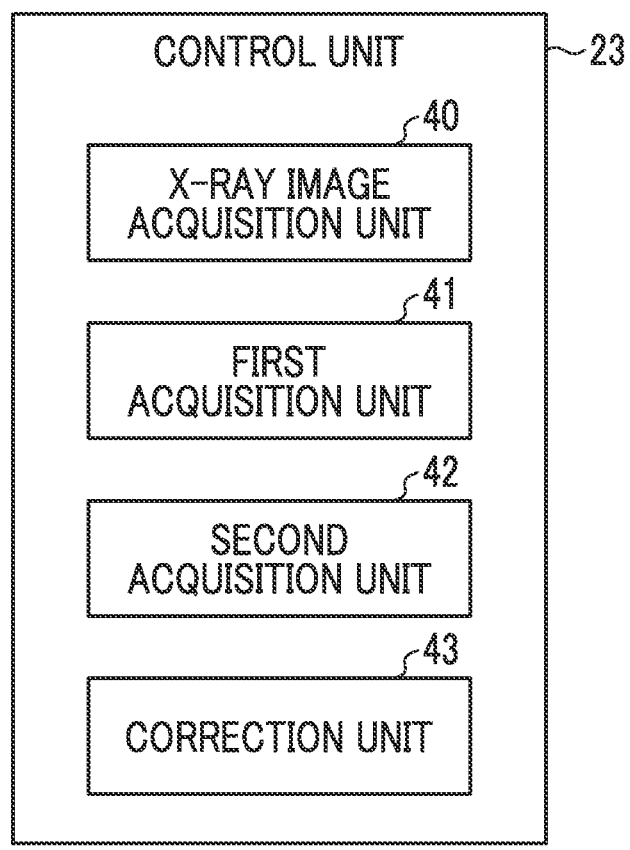
FIG. 6 is a block diagram showing a functional configuration of the control unit.

FIG. 6 is a block diagram showing a functional configuration of the control unit. As shown in FIG. 6, the control unit 23 includes an X-ray image acquisition unit 40, a first acquisition unit 41, a second acquisition unit 42, and a correction unit 43. The CPU 30 executes the operation program 34 to function as the X-ray image acquisition unit 40, the first acquisition unit 41, the second acquisition unit 42, and the correction unit 43.

The X-ray image acquisition unit 40 performs an operation during X-ray imaging performed in a state where the X-ray is irradiated. The X-ray image acquisition unit 40 drives the readout circuit 22 in a case where the pixel region 21 is irradiated with the X-ray generated by the X-ray source 10 via the subject to read out the pixel signal from the pixel region 21 in accordance with a predetermined readout mode. Then, the X-ray image acquisition unit 40 generates an X-ray image X0 based on the readout pixel signal. The generated X-ray image X0 is stored in the memory 32. In the present embodiment, the X-ray image acquisition unit 40 reads out the pixel signal from the pixel region 21 in a predetermined readout mode in a state where the X-ray is continuously irradiated by the irradiation switch 12 being continuously pressed to acquire the X-ray image X0 as a moving image.

Figure 7:
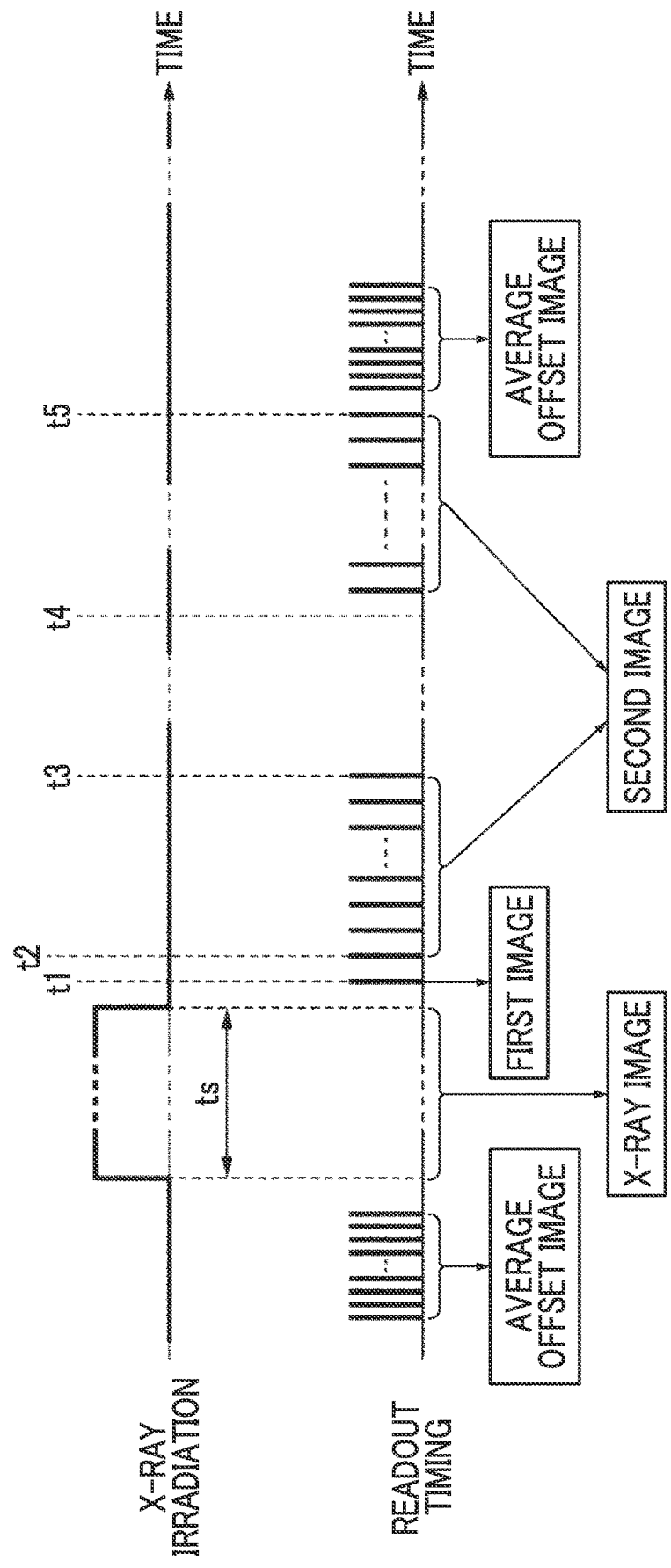
FIG. 7 is a diagram for describing processing performed by the control unit in a case of acquiring an image for correcting an X-ray image.

The first acquisition unit 41 and the second acquisition unit 42 perform processing of generating an image for correcting the X-ray image X0. FIG. 7 is a diagram for describing processing performed by the control unit in a case of acquiring an image for correcting an X-ray image. As shown in FIG. 7, the first acquisition unit 41 drives the readout circuit 22 in a state where the pixel region 21 is not irradiated with the X-ray before the electronic cassette 13 is irradiated with the X-ray to acquire the X-ray image X0 to repeatedly read out the pixel signal from the pixel region 21 a plurality of times in a predetermined readout mode. In FIG. 7, the readout timing is indicated by a line segment extending in a vertical direction. The number of times of readout may be set to 64, for example, but is not limited thereto. The first acquisition unit 41 and the second acquisition unit 42 constantly read out the pixel signal from the pixel region 21 in the readout mode while generating the image for correcting the X-ray image.

The first acquisition unit 41 performs averaging processing on the readout pixel signal to acquire an average offset image H0 based on the averaged pixel signal. The average offset image H0 represents a noise component consisting of dark current noise generated in each pixel of the pixel region 21 and fixed pattern noise generated by the charge amplifier or the like included in the readout circuit 22, that is, an offset component. The average offset image H0 is stored in the memory 32. A timing at which the first acquisition unit 41 generates the average offset image H0 is set to a sufficient time, for example, 180 seconds or more from the end of the irradiation of the pixel region 21 with the X-ray.

After the first acquisition unit 41 acquires the average offset image H0, the electronic cassette 13 is continuously irradiated with the X-ray to acquire the X-ray image of the subject. A continuous irradiation time is set to ts. Since the present embodiment relates to the processing of the correction of the X-ray image acquired by the imaging performed after the continuous irradiation, the description of the correction of the X-ray image in the continuous irradiation will not be described.

Figure 8:
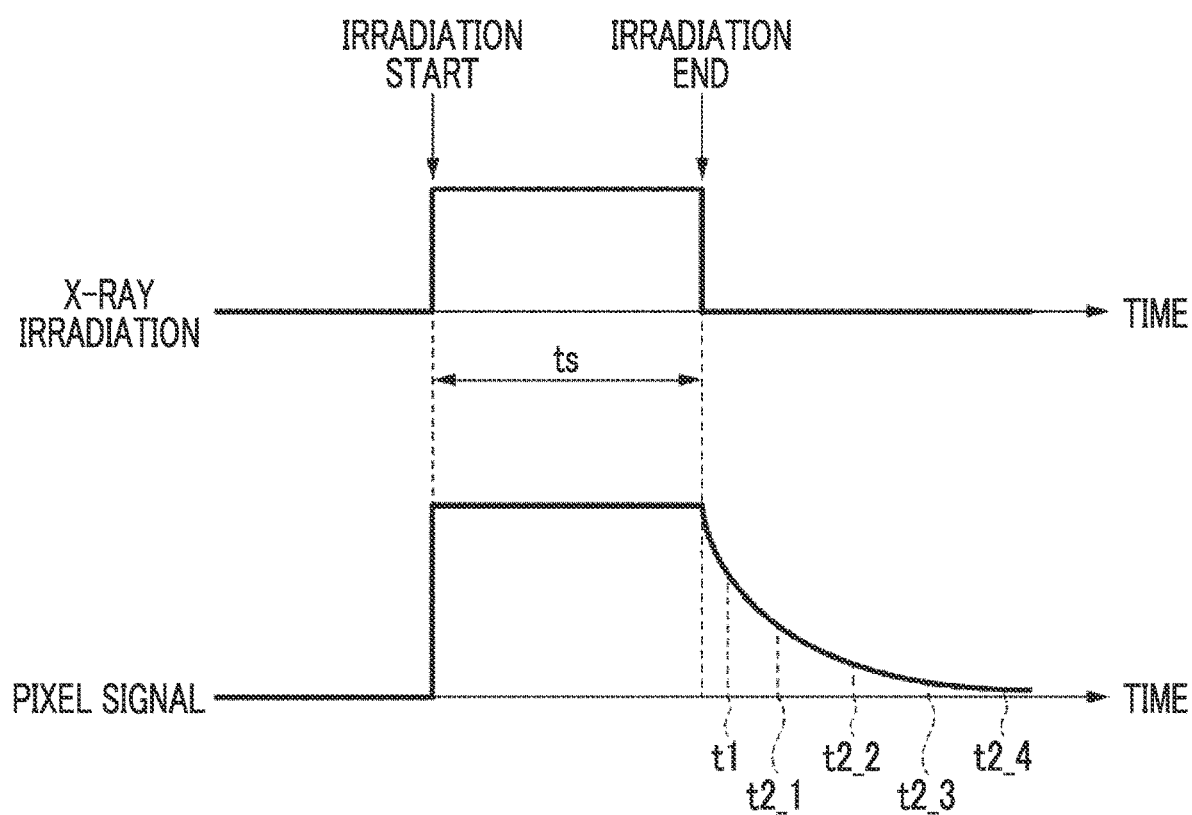
FIG. 8 is a diagram for describing a lag.

The pixel signal read out from the pixel region 21 after the end of the continuous irradiation of the X-ray includes an afterimage (lag) due to the continuous irradiation of the X-ray. FIG. 8 is a diagram for describing the lag. As shown in FIG. 8, while the pixel region 21 is irradiated with the X-ray, the pixel signal having a magnitude according to an X-ray dose is obtained from the pixel region 21. On the other hand, even in a case where the X-ray irradiation is stopped, the pixel signal obtained from the pixel region 21 does not immediately become zero, and the lag is included. As shown in FIG. 8, the lag decreases over time. The decrease in the lag is exponential, and a degree of attenuation is greater immediately after the irradiation is stopped.

The second acquisition unit 42 drives the readout circuit 22 in a state where the pixel region 21 is not irradiated with the X-ray when a first time t1 elapses from the end of the continuous irradiation of the X-ray to read out the pixel signal from the pixel region 21 in a predetermined readout mode for acquiring a first image H1. The first time t1, a second time t2 described below, and the like are measured by the timer 33.

Figure 9:
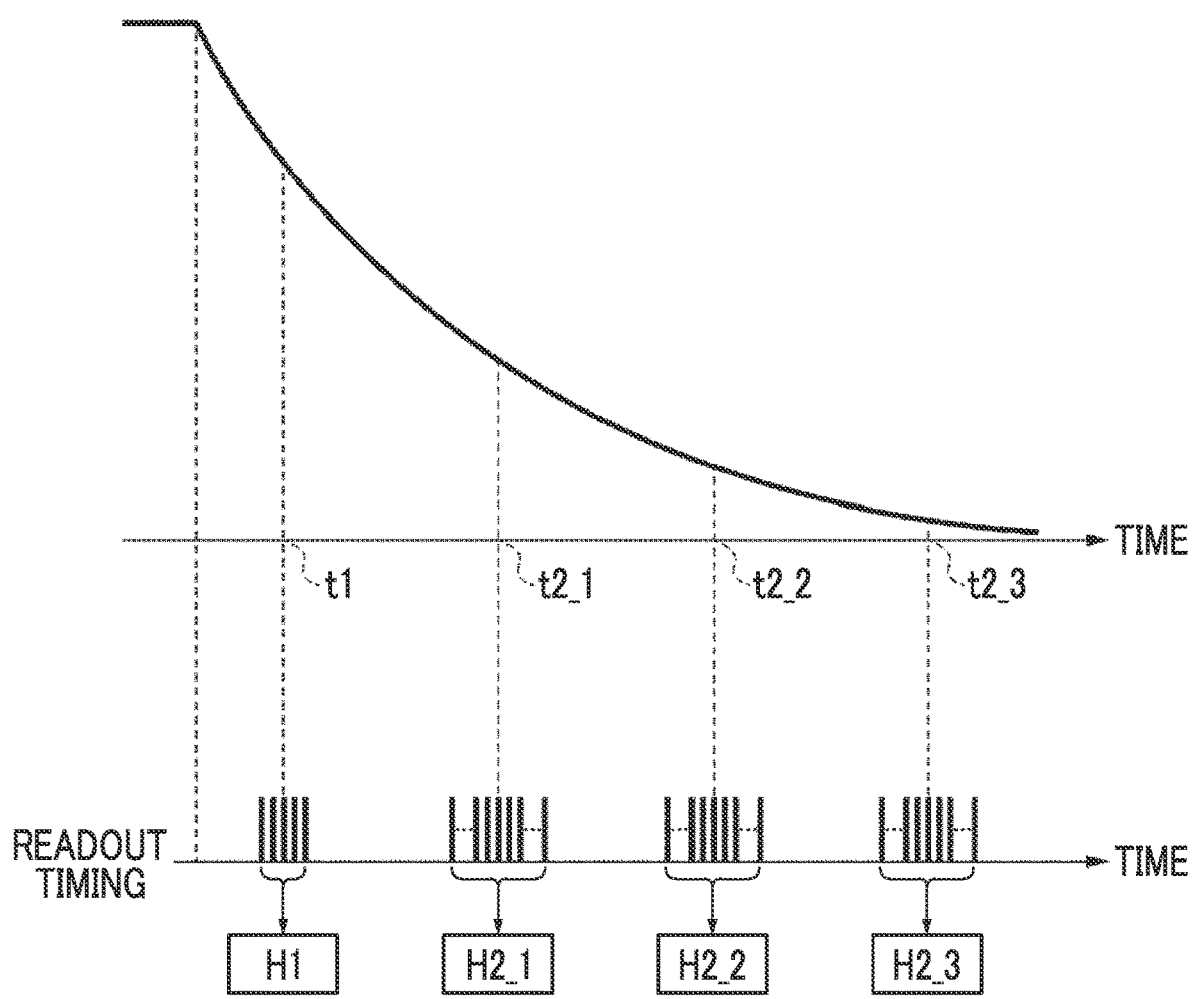
FIG. 9 is a diagram for describing readout of a pixel signal after an X-ray is continuously irradiated.

In the following description, the first time t1 and the second time t2 will be described with a time at which the continuous irradiation of the X-ray is ended as a starting point of a start time. The same applies to a third time t3, a fourth time t4, and a fifth time t5, which will be described below. Further, a relationship between the first to fifth times t1 to t5 is t1<t2<t3<t4<t5. FIG. 9 is a diagram for describing the readout of the pixel signal after the X-ray is continuously irradiated. As shown in FIG. 9, the second acquisition unit 42 reads out, from the pixel region 21, pixel signals for five times before and after the first time t1 from the end of the continuous irradiation of the X-ray.

That is, the second acquisition unit 42 reads out, from the pixel region 21, pixel signals for five frames in total of two frames immediately before the first time t1 elapses, one frame of the first time t1, and two frames immediately after the first time t1 has elapsed. In FIG. 9, the readout timing is indicated by a line segment extending in the vertical direction. The second acquisition unit 42 averages the pixel signals for five times to acquire the first image H1. With the averaging of the pixel signals in this manner, a granular component in the first image H1 can be reduced. The first image H1 represents a lag component and an offset component included in the pixel signal at a time point where the first time t1 elapses from the end of the X-ray irradiation. The first image H1 and the first time t1 are stored in the memory 32.

Further, the second acquisition unit 42 drives the readout circuit 22 in a state where the pixel region 21 is not irradiated with the X-ray when the second time (referred to as t2_1) elapses from the end of the continuous irradiation of the X-ray to read out the pixel signal from the pixel region 21 in a predetermined readout mode for acquiring the second image. Furthermore, the second acquisition unit 42 drives the readout circuit 22 in a state where the pixel region 21 is not irradiated with the X-ray when second times t2_2, t2_3, and the like elapse to repeatedly read out the pixel signal from the pixel region 21 in a predetermined readout mode for updating the second image. An interval between the second times t2_1, t2_2, t2_3, and the like may be identical to a time from the end of the continuous irradiation of the X-ray until the elapse of the second time t2_1. Since t1<t2<t3, t1<t2_1, t2_2, t2_3, and the like <t3.

In the present embodiment, the second acquisition unit 42 reads out, from the pixel region 21, pixel signals for 17 times at the second time t2 and before and after the second time t2 from the end of the continuous irradiation of the X-ray. That is, the second acquisition unit 42 reads out, from the pixel region 21, pixel signals for 17 frames in total of 8 frames immediately before the second times t2_1, t2_2, t2_3, and the like elapse from the end of the continuous irradiation of the X-ray, one frame of the second time t2_1, t2_2, t2_3, and the like, and 8 frames immediately after the second times t2_1, t2_2, t2_3, and the like have elapsed. In FIG. 9, all readout timings are not shown for the second time t2_1, t2_2, t2_3, and the like.

The second acquisition unit 42 averages the pixel signals for 17 times to acquire second images H2_1, H2_2, H2_3, and the like corresponding to the second times t2_1, t2_2, t2_3, and the like. With the averaging of the pixel signals in this manner, granular components in the second images H2_1, H2_2, H2_3, and the like can be reduced. The second images H2_1, H2_2, H2_3, and the like represent lag components and offset components included in the pixel signals at a time point where the second times t2_1, t2_2, t2_3, and the like elapses from the end of the X-ray irradiation. In the present embodiment, the second images H2_1, H2_2, H2_3, and the like are updated as described above, and the latest second image (referred to simply as H2) and the second time (referred to as t2) at which the latest second image is acquired are stored in the memory 32.

Figure 10:
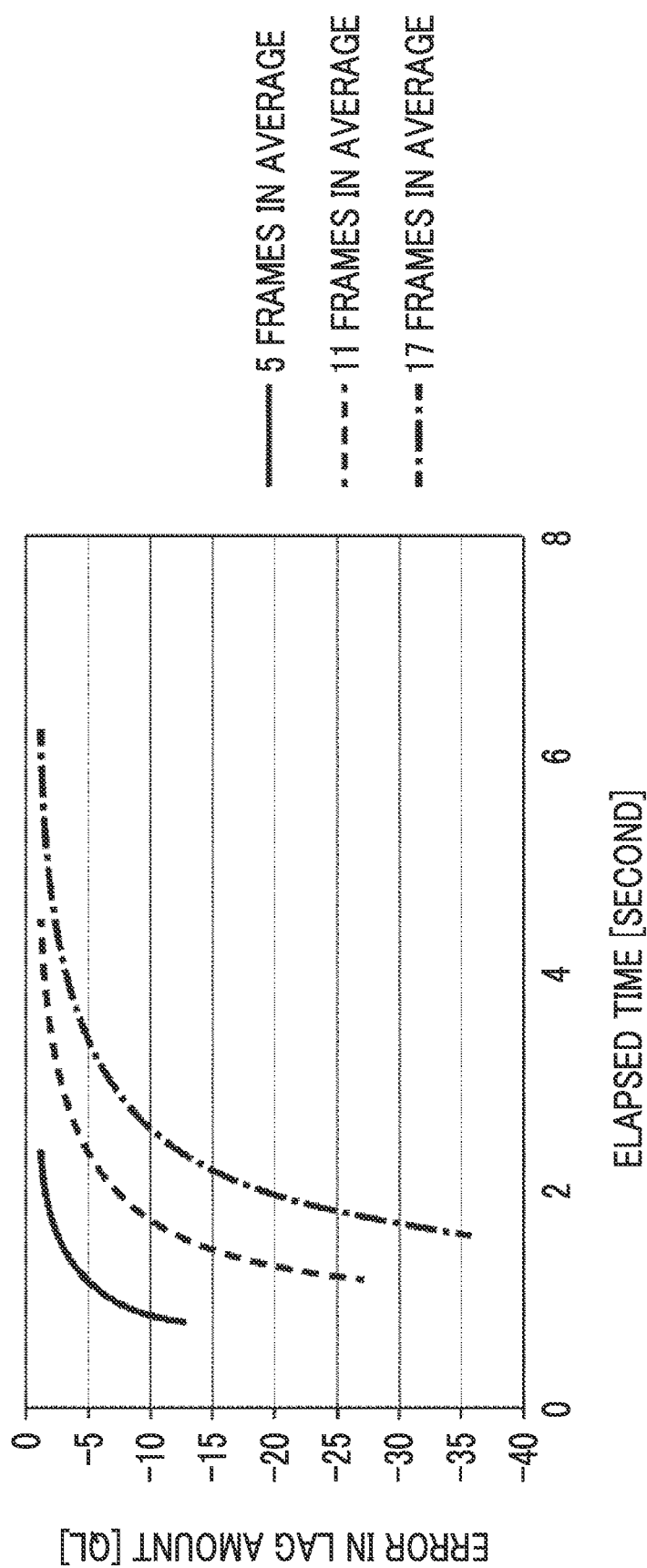
FIG. 10 is a graph showing a relationship between an elapsed time from an irradiation end and an error in a lag amount according to the number of frames used for averaging.

FIG. 10 is a graph showing a relationship between an elapsed time from the end of irradiation and an error in a lag amount according to the number of frames used for averaging in a case of acquiring the first image and the second image. In FIG. 10, the horizontal axis represents the elapsed time from the X-ray irradiation, the vertical axis represents the error in the lag amount, and the unit is quantum level (QL) representing a charge amount. By increasing the number of frames used for averaging, the granular component included in the pixel signal can be reduced. However, since an attenuation amount of the lag is large immediately after the end of the X-ray irradiation, in a case where the elapsed time from the end of the continuous irradiation of the X-ray is short, the error between the averaged lag and an actual lag becomes large as the number of frames to be averaged is larger.

Therefore, in the present embodiment, the number of frames of the pixel signal in a case of acquiring the first image H1 is reduced (5 frames), and the number of frames of the pixel signal in a case of acquiring the second image H2 is increased (17 frames). Further, the first time t1 is preferably the most recent time after the end of the continuous irradiation of the X-ray, for example, preferably within 4.5 seconds, more preferably within 2 seconds, and further more preferably 1.5 seconds. Further, the second time t2_1 for acquiring the second image H2_1 for the first time is preferably within 6 seconds from the end of the continuous irradiation of the X-ray.

In the present embodiment, the second acquisition unit 42 repeatedly updates the second image H2 until the third time t3 longer than the second time t2 elapses. After the elapse of the third time t3, the update of the second image H2 is stopped until the fourth time t4 longer than the third time t3 elapses. Further, the update of the second image H2 is restarted after the elapse of the fourth time t4, and the second image H2 is updated until the fifth time t5 longer than the fourth time t4 elapses. Furthermore, after the elapse of the fifth time t5, the second acquisition unit 42 stops the acquisition of the second image H2, and the first acquisition unit 41 updates the average offset image H0. The third time t3 can be set to, for example, 30 seconds, the fourth time t4 can be set to, for example, 90 seconds, and the fifth time t5 can be set to, for example, 180 seconds.

Figure 11:
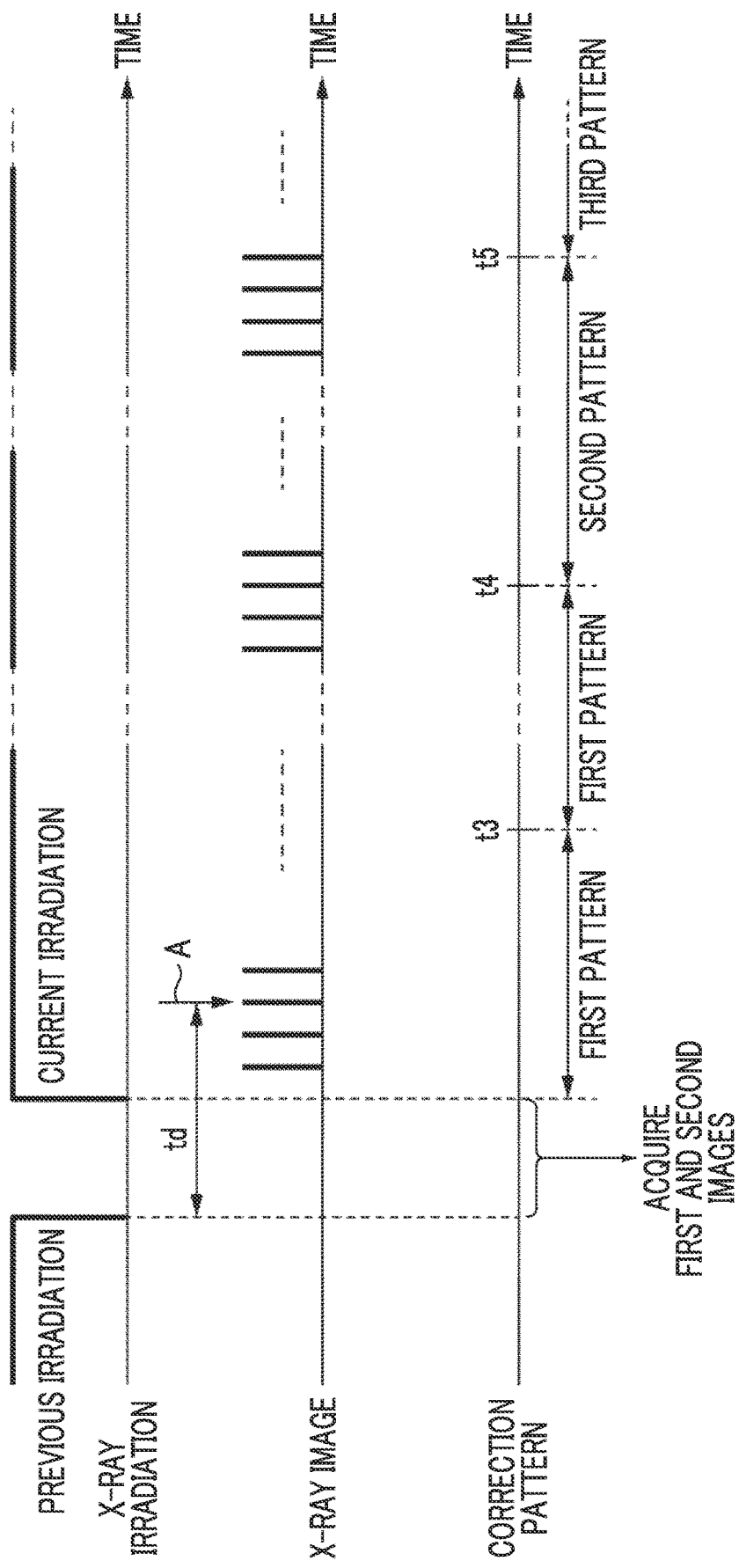
FIG. 11 is a diagram for describing X-ray irradiation, acquisition of an X-ray image, and correction according to the elapsed time from the end of X-ray continuous irradiation.

In a case where the X-ray image X0 is acquired by transmission imaging, the correction unit 43 acquires the image used for correcting the X-ray image X0 from the memory 32 according to an elapsed time from the end of previous continuous irradiation of the X-ray at the time of acquiring the X-ray image X0 and corrects the X-ray image X0 based on the acquired image. FIG. 11 is a diagram for describing the X-ray irradiation, the acquisition of the X-ray image X0, and the correction according to the elapsed time from the end of the X-ray continuous irradiation. In FIG. 11, an acquisition timing of the X-ray image X0 is indicated by a line segment extending in the vertical direction. In the present embodiment, as shown in FIG. 11, in a period during which the X-ray is not irradiated between the previous irradiation and the irradiation for acquiring the X-ray image X0 (referred to as current irradiation), the second acquisition unit 42 acquires the first image H1 and the second image H2. In a case where the imaging for acquiring the X-ray image is started, the second acquisition unit 42 stops the acquisition of the first image H1 and the second image H2.

The correction unit 43 performs the correction according to a first pattern on the X-ray image X0 acquired until the third time t3 longer than the second time t2 elapses from the end of the previous continuous irradiation of the X-ray. Further, the correction unit 43 also performs the correction according to the first pattern on the X-ray image X0 acquired until the fourth time t4 longer than the third time t3 elapses from the end of the previous continuous irradiation of the X-ray. Further, the correction unit 43 performs the correction by a second pattern on the X-ray image X0 acquired until the fifth time t5 longer than the fourth time t4 elapses from the end of the previous continuous irradiation of the X-ray. Further, the correction unit 43 performs the correction by a third pattern on the X-ray image X0 acquired after the elapse of the fifth time t5 from the end of the previous continuous irradiation. Hereinafter, the correction by each pattern will be described.

The correction unit 43 acquires, for the X-ray image X0 to be corrected, the previous continuous irradiation time is of the X-ray and the elapsed time from the end of the previous continuous irradiation of the X-ray at the time of acquiring the X-ray image X0 to be corrected. For example, in a case where the X-ray image to be corrected is acquired at a timing indicated by an arrow A in FIG. 11, an elapsed time td from the end of the previous continuous irradiation of the X-ray to the timing indicated by the arrow A is acquired. The acquired elapsed time td is referred to as a defined time. The X-ray image X0 to be corrected is acquired when the defined time td elapses from the end of the previous continuous irradiation of the X-ray.

Therefore, for the X-ray image X0 acquired until the third time t3 longer than the second time t2 elapses from the end of the previous continuous irradiation of the X-ray, the defined time td is the third time t3 or less. Further, for the X-ray image X0 acquired until the fourth time t4 longer than the third time t3 elapses from the end of the previous continuous irradiation, the defined time td exceeds the third time t3 and is the fourth time t4 or less. Further, for the X-ray image X0 acquired until the fifth time t5 longer than the fourth time t4 elapses from the end of the previous continuous irradiation, the defined time td exceeds the fourth time t4 and is the fifth time is t5 or less. Further, for the X-ray image X0 acquired after the elapse of the fifth time t5 from the end of the previous continuous irradiation, the defined time td exceeds the fifth time t5.

First, the first pattern will be described. In a case where the defined time td is the fourth time t4 or less, the correction unit 43 generates the continuous irradiation time ts of the X-ray, the first time t1, the second time t2 at which the latest second image H2 stored in the memory 32 is acquired, and an offset image F1 representing the offset component and a lag image L1 representing the lag component according to the defined time td, based on the first image H1 and the latest second image H2 and the average offset image H0 stored in the memory 32.

Specifically, in a case where the defined time td is the fourth time t4 or less, the correction unit 43 generates the offset image F1 and the lag image L1 by the following equations (1) and (2) using two coefficients α1 and α2 according to the first image H1, the second image H2, and the average offset image H0 and the continuous irradiation time ts, the first time t1, the second time t2, and the defined time td. In equations (1) and (2), M[ ] indicates filtering by a median filter. A size of the median filter can be, for example, 19×19, but is not limited thereto. Further, although equations (1) and (2) and equations (3) to (6) described below are calculations using an image, (x,y) representing a pixel position in the image is omitted.

$$F1 = M[\alpha 2 \times H1 + (1-\alpha 2) \times H2 - H0] \quad (1)$$

$$L1 = M[-\alpha 1 \times (1-\alpha 2) \times (H1 - H2)] \quad (2)$$

In equations (1) and (2), $$\alpha 1 = -(td/t1)^\gamma$$

$$\alpha 2 = -(t2/t1))^\gamma / \{1 - (t2/t1))^\gamma\}$$

γ is a coefficient that determines attenuation behavior according to the previous continuous irradiation time ts of the X-ray. ")^" represents exponentiation. In the present embodiment, a relationship between the continuous irradiation time ts of the X-ray and the coefficient γ is stored in the memory 32 as a table, and the correction unit 43 refers to this table to acquire the coefficient γ according to the continuous irradiation time ts.

The correction unit 43 corrects the X-ray image X0 by the following equation (3) to generate a corrected X-ray image X1. Accordingly, the offset component and the lag component included in the X-ray image X0 can be removed. Since the offset image F1 and the lag image L1 are generated by performing the filtering processing by the median filter as shown in equations (1) and (2), the granularity is improved. However, a high frequency component of noise generated in a pixel unit of the pixel region 21 is lost. Therefore, with the generation of the corrected X-ray image X1 by using the average offset image H0 as shown in equation (3), it is possible to correct the high frequency component of the noise generated in the pixel unit of the pixel region 21.

$$X1 = X0 - H0 - F1 - L1 \quad (3)$$

In a case where the defined time td is the third time t3 or less, the X-ray image X0 includes the offset component and the lag component. Therefore, with the generation of the offset image F1 and the lag image L1 from the first image H1 and the second image H2 by equations (1) to (3), it is possible to accurately separate the offset component and the lag component from the X-ray image X0.

On the other hand, in a case where the defined time td exceeds the third time t3, the lag component included in the X-ray image X0 decreases and the dark current noise due to heat increases. Thus, the offset component increases. As a result, it is not possible to accurately separate the offset component and the lag component included in the X-ray image X0.

Therefore, in the present embodiment, the second acquisition unit 42 stops the updating of the second image H2 in a case where the third time t3 is exceeded after the previous continuous irradiation of the X-ray. On the other hand, the lag component included in the X-ray image X0 does not become zero. Therefore, in a case where the defined time td exceeds the third time t3 and is the fourth time t4 or less, in the present embodiment, the offset image F1 and the lag image L1 are generated from the first image H1 and the second image H2 updated when the third time t3 elapses by equations (1) to (3) to separate the offset component and the lag component from the X-ray image X0.

Since the pixel signal is read out from the pixel region 21 even while the update of the second image H2 is stopped, the dark current noise due to the heat is further increased and thus the accuracy of the correction is lowered. Therefore, in the present embodiment, in a case where the fourth time t4 is exceeded from the end of the previous continuous irradiation of the X-ray, the second acquisition unit 42 restarts the update of the second image H2 to perform the correction according to the second pattern described below. The offset component is dominant in the second image H2 acquired after the restart of the update.

Next, the second pattern will be described. In a case where the defined time td is equal to or less than the fifth time t5 longer than the fourth time t4, the correction unit 43 generates an offset image F2 based on the latest second image H2 and the average offset image H0 stored in the memory 32. Specifically, the correction unit 43 uses the second image H2 and the average offset image H0 to generate the offset image F2 by the following equation (4).

$$F2 = M[H2 - H0] \quad (4)$$

The correction unit 43 corrects the X-ray image X0 by the following equation (5) to generate the corrected X-ray image X1. The reason for using the average offset image H0 in equation (5) is the same as in equation (3).

$$X1 = X0 - H0 - F2 \quad (5)$$

In a case where the defined time td elapses from the fourth time t4, the lag component included in the X-ray image X0 decreases, but the dark current noise due to the heat increases. Thus, the offset component increases. As a result, it is not possible to accurately separate the offset component and the lag component included in the X-ray image X0. Therefore, in the present embodiment, in a case where the defined time td elapses from the fourth time t4, the offset image F2 is obtained by using only the second image H2 according to the second pattern to correct the X-ray image X0.

Next, the third pattern will be described. In a case where the defined time td exceeds the fifth time t5, the lag component included in the X-ray image X0 can be ignored. Thus, the X-ray image X0 can be regarded as including only the offset component. Therefore, in a case where the defined time exceeds the fifth time t5 by the following equation (6), the correction unit 43 corrects the X-ray image X0 based on the average offset image H0 to generate the corrected X-ray image X1.

$$X1 = X0 - H0 \quad (6)$$

Figure 12:
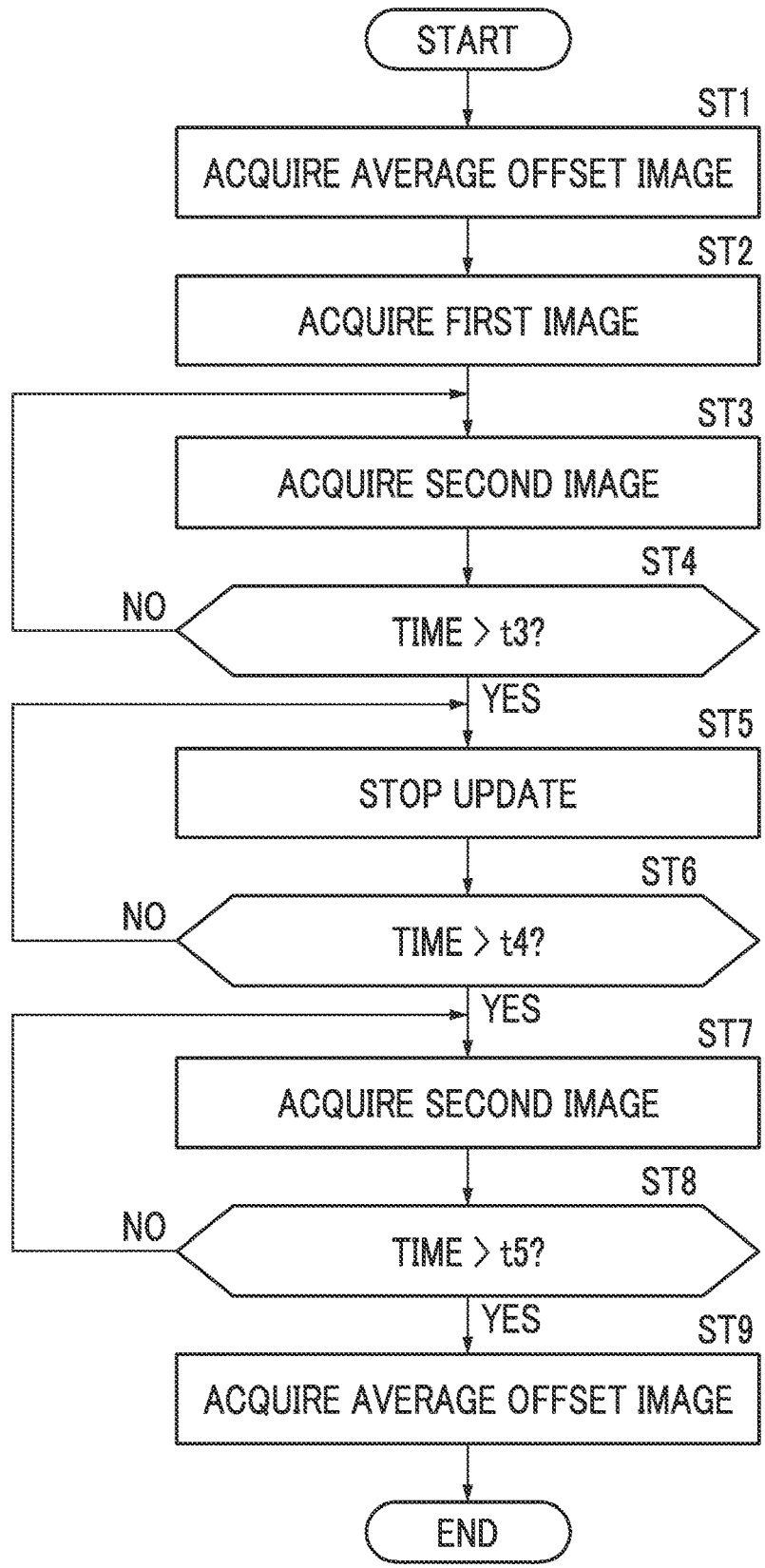
FIG. 12 is a flowchart showing processing of generating an image for correcting the X-ray image.

Next, processing performed in the present embodiment will be described. First, processing of acquiring the image for correcting the X-ray image will be described. FIG. 12 is a flowchart showing the processing of acquiring the image for correcting the X-ray image. In response to an instruction to start the processing, the first acquisition unit 41 acquires the average offset image H0 in a state where the electronic cassette 13 is not irradiated with the X-ray and stores the acquired image in the memory 32 (step ST1).

Next, in a case where the irradiation switch 12 is pressed to continuously irradiate the electronic cassette 13 with the X-ray and then the continuous irradiation ends, the second acquisition unit 42 acquires the first image H1 in a state where the pixel region 21 is not irradiated with the X-ray when the first time t1 elapses from the end of the continuous radiation of the X-ray and stores the acquired image in the memory 32 (step ST2). Further, the second acquisition unit 42 acquires the second image H2 in a state where the pixel region 21 is not irradiated with the X-ray when the second time t2 elapses from the end of the continuous irradiation of the X-ray and stores the acquired image in the memory 32 (step ST3).

Next, the second acquisition unit 42 determines whether or not the time from the end of the continuous irradiation of the X-ray exceeds the third time t3 (step ST4). In a case where step ST4 is negative, the processing returns to step ST3 to repeat the processing of steps ST3 and ST4. Accordingly, the updated second image H2 is stored in the memory 32. In a case where step ST4 is affirmed, the second acquisition unit 42 stops the update of the second image H2 (step ST5).

Next, the second acquisition unit 42 determines whether or not the time from the end of the continuous irradiation of the X-ray exceeds the fourth time t4 (step ST6). In a case where step ST6 is negative, the processing returns to step ST5 to repeat the processing of steps ST5 and ST6. Accordingly, the update of the second image H2 continues to be stopped. Therefore, the latest second image H2 stored in the memory 32 is acquired at the time point of the third time t3.

In a case where step ST6 is affirmed, the second acquisition unit 42 restarts the update of the second image H2, acquires the second image H2, and stores the acquired image in the memory 32 (step ST7). Subsequently, the second acquisition unit 42 determines whether or not the time from the end of the continuous irradiation of the X-ray exceeds the fifth time t5 (step ST8). In a case where step ST8 is negative, the processing returns to step ST7 to repeat the processing of steps ST7 and ST8. Accordingly, the updated second image H2 is stored in the memory 32. In a case where step ST8 is affirmed, the second acquisition unit 42 stops the acquisition of the second image H2, the first acquisition unit 41 acquires the average offset image H0 (step ST9), and the processing of acquiring the image for correcting the X-ray image ends.

In the processing of acquiring the image for correcting the X-ray image shown in FIG. 12, in a case where the imaging of the X-ray image X0 is started, the second acquisition unit 42 stops the processing of acquiring the image. Accordingly, the second image H2 acquired in a case where the processing is stopped is stored in the memory 32.

Figure 13:
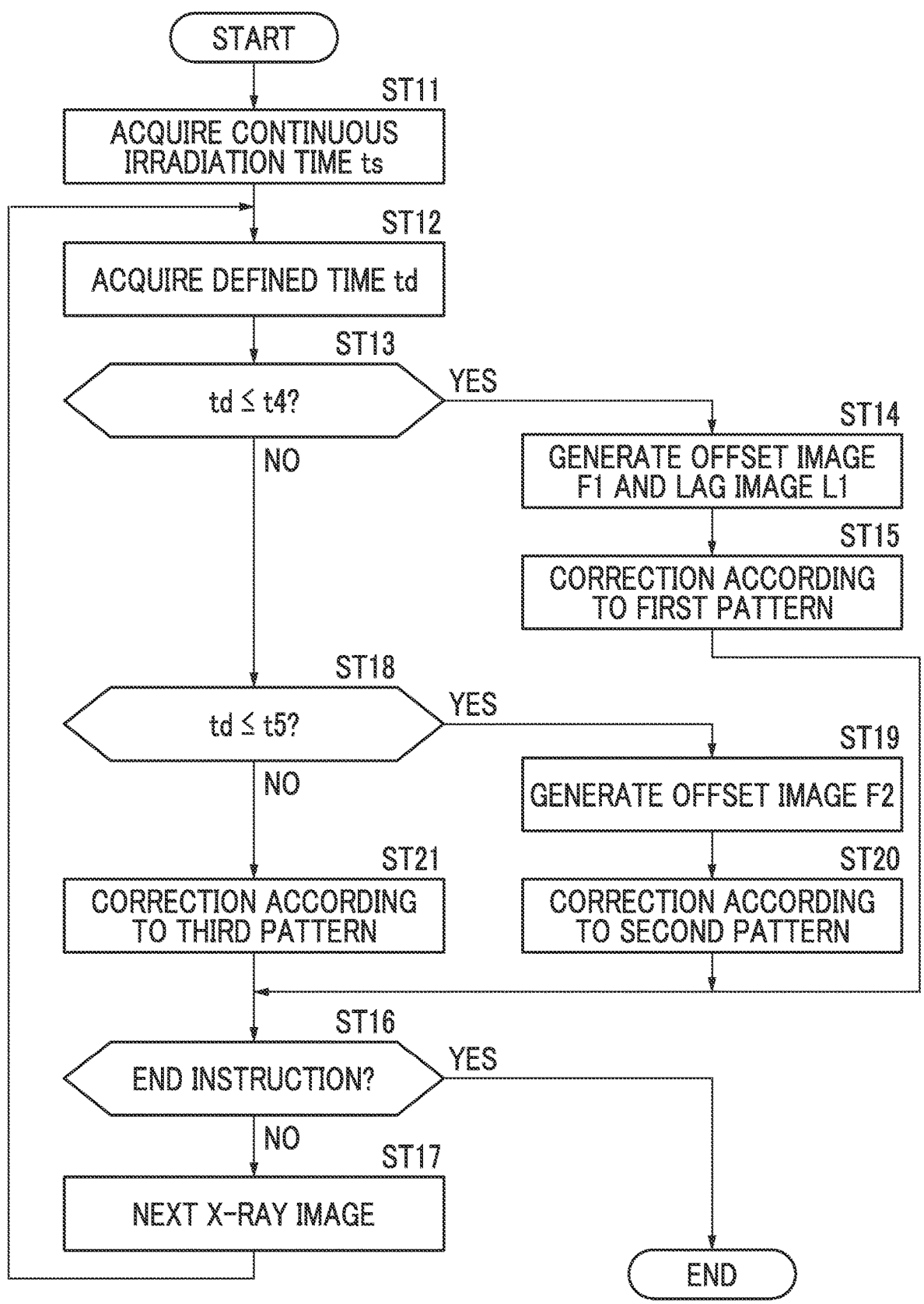
FIG. 13 is a flowchart showing processing of correcting the X-ray image.

FIG. 13 is a flowchart showing processing of correcting the X-ray image. The X-ray image X0 is continuously acquired by the X-ray image acquisition unit 40 in a predetermined readout mode. Further, the processing shown in FIG. 13 is started by starting the processing of acquiring the X-ray image X0. The correction unit 43 acquires the previous continuous irradiation time is of the X-ray for the X-ray image X0 to be corrected (step ST11) and acquires the elapsed time, that is, the defined time td from the end of the previous continuous irradiation of the X-ray in a case where the X-ray image X0 is acquired (step ST12).

The correction unit 43 determines whether or not the defined time td is the fourth time t4 or less (step ST13). In a case where step ST13 is affirmed, the correction unit 43 generates the offset image F1 representing the offset component and the lag image L1 representing the lag component according to the continuous irradiation time ts of the X-ray, the first time t1, the second time t2, and the defined time td, based on the first image H1, the second image H2, and the average offset image H0 (step ST14).

The correction unit 43 corrects the X-ray image X0 according to the first pattern to generate the corrected X-ray image X1 (step ST15). Subsequently, the correction unit 43 determines whether or not there is an instruction to end the processing of acquiring the X-ray image (step ST16). In a case where step ST16 is negative, the X-ray image to be corrected is changed to a next X-ray image (step ST17), and the processing returns to the processing of step ST12. In a case where step ST16 is affirmed, the processing ends.

On the other hand, in a case where step ST13 is negative, the correction unit 43 determines whether or not the defined time td is the fifth time t5 or less (step ST18). In a case where step ST18 is affirmed, the offset image F2 is generated based on the second image H2 and the average offset image H0 (step ST19). Then, the correction unit 43 corrects the X-ray image X0 according to the second pattern to generate the corrected X-ray image X1 (step ST20), and the processing proceeds to the processing of step ST16.

In a case where step ST18 is negative, the correction unit 43 corrects the X-ray image X0 according to the third pattern based on the average offset image H0 to generate the corrected X-ray image X1 (step ST21), and the processing proceeds to ST16. In a case where step ST16 is affirmed, the processing ends.

Accordingly, the corrected X-ray images X1 are sequentially acquired, and the X-ray images X1 are displayed on the display 14B as moving images.

As described above, in the present embodiment, the X-ray image X0 is corrected according to the continuous irradiation time ts of the X-ray, the first time t1, the second time t2, and the defined time td, based on the first image H1, the second image H2, and the average offset image H0. Therefore, it is possible to improve the accuracy of the offset correction and to suppress the influence of the afterimage in a case where the X-ray image X0 is corrected.

On the other hand, in a case where the pixel signal is read out from the pixel region 21, a plurality of readout modes may be switched and used. In this case, the first acquisition unit 41 may be configured to continuously generate the average offset image corresponding to each of the plurality of readout modes while switching the plurality of readout modes. The second acquisition unit 42 may be configured to continuously acquire the first image H1 corresponding to each of the plurality of readout modes while switching the plurality of readout modes.

Figure 14:
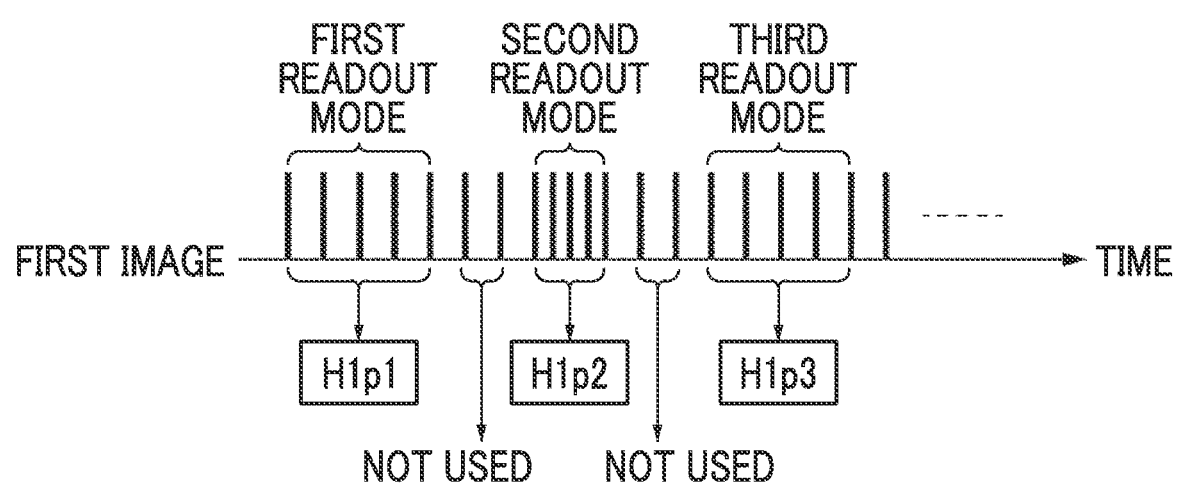
FIG. 14 is a diagram for describing a timing of acquiring a first image while switching a plurality of readout modes.

FIG. 14 is a diagram for describing a timing of acquiring the first image H1 while switching the plurality of readout modes. As shown in FIG. 14, the second acquisition unit 42 first reads out the pixel signals for five frames from the pixel region 21 in the first readout mode to acquire a first image H1p1 in the first readout mode. Next, the second acquisition unit 42 reads out the pixel signals for five frames from the pixel region 21 in the second readout mode to acquire a first image H1p2 in the second readout mode. Further, the second acquisition unit 42 reads out the pixel signals for five frames from the pixel region 21 in the third readout mode to acquire a first image H1p3 in the third readout mode.

Since the readout mode is not completely switched at the time of switching the readout mode, the readout rate and the readout method are not stable. Therefore, the second acquisition unit 42 acquires the first images H1p1, H1p2, and H1p3 using pixel signals other than the pixel signals read out from the pixel region 21 at the time of switching the readout mode. Specifically, as shown in FIG. 14, the first images H1p1, H1p2, and H1p3 are acquired without using the pixel signals for two frames acquired during the switching of the readout mode. Accordingly, it is possible to acquire the appropriate first images H1p1, H1p2, and H1p3 according to the readout mode.

After the acquisition of the first image, the second acquisition unit 42 repeats the continuous acquisition of the second image corresponding to each of the plurality of readout modes while switching the plurality of readout modes. FIG. 15 is a diagram for describing a timing of acquiring the second image while switching the plurality of readout modes. As shown in FIG. 15, the second acquisition unit 42 first reads out the pixel signals for 17 frames from the pixel region 21 in the first readout mode to acquire a second image 2_1p1 in the first readout mode. Next, the second acquisition unit 42 reads out the pixel signals for 17 frames from the pixel region 21 in the second readout mode to acquire a second image H2_1p2 in the second readout mode. Further, the second acquisition unit 42 reads out the pixel signals for 17 frames from the pixel region 21 in the third readout mode to acquire a second image H2_1p3 in the third readout mode.

Subsequently, the second acquisition unit 42 reads out the pixel signals for 17 frames from the pixel region 21 in the first readout mode to acquire a second image H2_2p1 in the first readout mode. Next, the second acquisition unit 42 reads out the pixel signals for 17 frames from the pixel region 21 in the second readout mode to acquire a second image H2_2p2 in the second readout mode. Further, the second acquisition unit 42 reads out the pixel signals for 17 frames from the pixel region 21 in the third readout mode to acquire a second image H2_2p3 in the third readout mode. The second acquisition unit 42 repeats such readout to acquire the second image corresponding to each of the plurality of readout modes.

Also in a case where the second image is acquired, the second image may be acquired by using a pixel signal other than the pixel signal read out from the pixel region 21 at the time of switching the readout mode. Specifically, as shown in FIG. 15, the second image is acquired without using the pixel signals for two frames acquired during the switching of the readout mode. Accordingly, it is possible to acquire an appropriate second image corresponding to the readout mode.

In a case where the X-ray image is acquired, the same readout mode is continuously used in many cases. Therefore, in a case where the first image and the second image are acquired by the plurality of readout modes, the readout mode used first is preferably the readout mode used for reading out the pixel signal from the previous pixel region 21.

In the above embodiment, the second image H2 is updated, but the second image H2 may not be updated. In this case, the generation of the offset image and the lag image and the correction of the X-ray image X0 are performed by using the second image H2 acquired in the second time t2.

The radiation used in the above embodiment is not limited to the X-ray and can be applied to a system in which the subject is imaged by using another radiation such as γ-ray.

In the above embodiment, as a hardware structure of the processing units that execute various types of processing such as the X-ray image acquisition unit 40, the first acquisition unit 41, the second acquisition unit 42, and the correction unit 43, the following various processors can be used. The various processors include a programmable logic device (PLD) which is a processor whose circuit configuration is changeable after manufacturing such as a field programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (program) to function as various processing units, as described above.

One processing unit may be configured by one of the various processors or a combination of two or more processors of the same type or different types (for example, a combination of a plurality of FPGAs or a combination of a CPU and an FPGA). The plurality of processing units may be configured of one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

Further, more specifically, a circuitry combining circuit elements such as semiconductor elements can be used as the hardware structure of the various processors.

What is claimed is:

1. A radiation detection device comprising:
a pixel region in which a plurality of pixels for detecting a radiation are arranged;
a readout unit that reads out a pixel signal from the pixel region; and
at least one processor,
wherein the processor is configured to:
average a plurality of images acquired by reading out a pixel signal from the pixel region a plurality of times in a state where irradiation with the radiation is not performed to acquire an average offset image;
perform continuous irradiation with the radiation for imaging a subject on the pixel region and read out the pixel signal from the pixel region when a first time elapses from an end of the continuous irradiation to acquire a first image;
read out the pixel signal from the pixel region when a second time longer than the first time elapses from the end of the continuous irradiation to acquire a second image;
perform irradiation with the radiation for imaging the subject on the pixel region after an elapse of a defined time from the end of the continuous irradiation and read out the pixel signal from the pixel region to acquire a radiographic image; and
generate an offset image representing an offset component and an afterimage image representing an afterimage component according to a time of the continuous irradiation, the first time, the second time, and the defined time, based on the first image, the second image, and the average offset image.

2. The radiation detection device according to claim 1,
wherein the processor repeatedly reads out the pixel signal from the pixel region after the acquisition of the first image to update the second image, and
generates the offset image and the afterimage image according to the time of the continuous irradiation, the first time, an updated second time until the updated second image is acquired from the end of the continuous irradiation, and the defined time, based on the first image, the updated second image, and the average offset image.

3. The radiation detection device according to claim 2,
wherein the processor continuously updates the second image until a third time longer than the second time elapses from the end of the continuous irradiation, stops the update of the second image until a fourth time longer than the third time elapses after the elapse of the third time, restarts the update of the second image after the elapse of the fourth time, updates the second image until a fifth time longer than the fourth time elapses, and stops the acquisition of the second image after the elapse of the fifth time to update the average offset image.

4. The radiation detection device according to claim 3,
wherein the processor generates the offset image and the afterimage image according to the time of the continuous irradiation, the first time, the second time, and the defined time, based on the first image, the second image, and the average offset image, in a case where the defined time is the fourth time or less, and
generates the offset image based on the second image and the average offset image in a case where the defined time exceeds the fourth time and is the fifth time or less.

5. The radiation detection device according to claim 3,
wherein the processor corrects the radiographic image based on the average offset image, the offset image, and the afterimage image to generate a corrected radiographic image in a case where the defined time is the fourth time or less,
corrects the radiographic image based on the average offset image and the afterimage image to generate a corrected radiographic image in a case where the defined time exceeds the fourth time and is the fifth time or less, and corrects the radiographic image based on the average offset image to generate a corrected radiographic image in a case where the defined time exceeds the fifth time.

6. The radiation detection device according to claim 5, wherein the processor outputs the corrected radiographic image for display.

7. The radiation detection device according to claim 2, wherein in a case where a plurality of readout modes in which a readout rate of the pixel signal and a readout method of the pixel signal from the pixel region are different from each other are set, the processor continuously acquires the average offset image corresponding to each of the plurality of readout modes while switching the plurality of readout modes, continuously acquires the first image corresponding to each of the plurality of readout modes while switching the plurality of readout modes, and updates the second image corresponding to each of the plurality of readout modes while switching the plurality of readout modes after the acquisition of the first image.

8. The radiation detection device according to claim 7, wherein the processor continuously acquires the first image while switching the plurality of readout modes in order from a readout mode used in previous radiation irradiation among the plurality of readout modes.

9. The radiation detection device according to claim 7, wherein the processor acquires the first image and the second image by using a pixel signal other than the pixel signal read out from the pixel region at the time of switching the readout mode.

10. The radiation detection device according to claim 1, wherein the processor reads out pixel signals from the pixel region a plurality of first number of times before and after the first time and averages the pixel signals read out the first number of times to acquire the first image, and reads out pixel signals from the pixel region a second number of times larger than the first number of times before and after the second time and averages the pixel signals read out the second number of times to acquire the second image.

11. An operation method in a radiation detection device including a pixel region in which a plurality of pixels for detecting a radiation are arranged, and a readout unit that reads out a pixel signal from the pixel region, the operation method comprising:

averaging a plurality of images acquired by reading out a pixel signal from the pixel region a plurality of times in a state where irradiation with the radiation is not performed to acquire an average offset image;

performing continuous irradiation with the radiation for imaging a subject on the pixel region and reading out the pixel signal from the pixel region when a first time elapses from an end of the continuous irradiation to acquire a first image;

reading out the pixel signal from the pixel region when a second time longer than the first time elapses from the end of the continuous irradiation to acquire a second image;

performing irradiation with the radiation for imaging the subject on the pixel region after an elapse of a defined time from the end of the continuous irradiation and reading out the pixel signal from the pixel region to acquire a radiographic image; and generating an offset image representing an offset component and an afterimage image representing an afterimage component according to a time of the continuous irradiation, the first time, the second time, and the defined time, based on the first image, the second image, and the average offset image.

12. A non-transitory computer-readable storage medium that stores an operation program for causing a computer to execute an operation method in a radiation detection device including a pixel region in which a plurality of pixels for detecting a radiation are arranged, and a readout unit that reads out a pixel signal from the pixel region, the operation program for causing the computer to execute:

a procedure of averaging a plurality of images acquired by reading out a pixel signal from the pixel region a plurality of times in a state where irradiation with the radiation is not performed to acquire an average offset image;

a procedure of performing continuous irradiation with the radiation for imaging a subject on the pixel region and reading out the pixel signal from the pixel region when a first time elapses from an end of the continuous irradiation to acquire a first image;

a procedure of reading out the pixel signal from the pixel region when a second time longer than the first time elapses from the end of the continuous irradiation to acquire a second image;

a procedure of performing irradiation with the radiation for imaging the subject on the pixel region after an elapse of a defined time from the end of the continuous irradiation and reading out the pixel signal from the pixel region to acquire a radiographic image; and a procedure of generating an offset image representing an offset component and an afterimage image representing an afterimage component according to a time of the continuous irradiation, the first time, the second time, and the defined time, based on the first image, the second image, and the average offset image.

* * * * *